(12) United States Patent
Roth

(10) Patent No.: US 12,311,358 B2
(45) Date of Patent: May 27, 2025

(54) MICROBIOLOGY TEST CARD

(71) Applicant: Roth Biosciences, LLC, Goshen, IN (US)

(72) Inventor: Jonathan N. Roth, Goshen, IN (US)

(73) Assignee: Roth Biosciences, LLC, Goshen, IN (US)

(*) Notice: Subject to any disclaimer, the term of this patent is extended or adjusted under 35 U.S.C. 154(b) by 0 days.

(21) Appl. No.: 17/803,380

(22) Filed: Jun. 6, 2022

(65) Prior Publication Data

US 2023/0390761 A1 Dec. 7, 2023

(51) Int. Cl.
*B01L 3/00* (2006.01)
*C12Q 1/04* (2006.01)

(52) U.S. Cl.
CPC .............. *B01L 3/5023* (2013.01); *C12Q 1/04* (2013.01); *B01L 2200/16* (2013.01); *B01L 2300/069* (2013.01); *B01L 2300/0816* (2013.01)

(58) Field of Classification Search
CPC .............. B01L 3/5023; B01L 2200/16; B01L 2300/069; B01L 2300/0816; C12Q 1/04
See application file for complete search history.

(56) References Cited

U.S. PATENT DOCUMENTS

| 6,022,682 | A | * | 2/2000 | Mach | ...................... | C12Q 1/14 |
|---|---|---|---|---|---|---|
| | | | | | | 435/805 |
| 2016/0018298 | A1 | * | 1/2016 | Roth | ..................... | B01L 3/5085 |
| | | | | | | 73/64.56 |
| 2017/0269074 | A1 | * | 9/2017 | Guirguis | .......... | G01N 33/54389 |

OTHER PUBLICATIONS

Jiahui Sun, Jia Huang, Yulong Li, Junwei Lv, Xianting Ding, A simple and rapid colorimetric bacteria detection method based on bacterial inhibition of glucose oxidase-catalyzed reaction, Talanta, vol. 197, pp. 304-309, May 15, 2019. (Year: 2019).*
Merck, Pathogen Detection, MC Media Pad, May 11, 2021. (Year: 2021).*
Kwi Nam Han, Jong-Soon Choi, Joseph Kwon, Three-dimensional paper-based slip device for one-step point-of-care testing, Scientific Reports, vol. 6, 25710, Feb. 10, 2016. (Year: 2016).*
Peter Q. Nguyen, et al., Wearable materials with embedded synthetic biology sensors for biomolecule detection, Nature Biotechnology, vol. 39, pp. 1366-1374, Nov. 2021. (Year: 2021).*

(Continued)

*Primary Examiner* — Gailene Gabel
(74) *Attorney, Agent, or Firm* — Gardner, Linn, Burkhart & Ondersma LLP

(57) ABSTRACT

A card is provided for detecting the existence and/or identity of microbial presence, having a base for receiving thereon a fluidic sample, a transparent cover to overlay the base, formed with a top layer, a bottom layer, and an adhesive layer therebetween, wherein a portion of the bottom layer is formed such that a portion of the adhesive layer is not covered by the bottom layer, and a media applied is to and retained by that portion of the adhesive layer which is not covered by the bottom layer, that media serving to gel the fluidic sample and/or support growth of a micro-organism whose existence and/or identity is being tested by the card. To facilitate manual and/or automated counting of visual indications of micro-organisms, a black ink grid system can be applied which does not diffuse in the presence of the fluidic sample and/or the media, but at the same time which readily is removable from the base when removal is desired.

12 Claims, 3 Drawing Sheets

(56) References Cited

OTHER PUBLICATIONS

Calvin M. Kunin and William J. Buesching, Novel Screening Method for Urine Cultures Using a Filter Paper Dilution System, Journal of Clinical Microbiology, vol. 8, No. 3, pp. 1187-1190, Mar. 2000. (Year: 2000).*

Kim et al., One-step sensing of foodborne pathogenic bacteria using a 3D paper-based device, The Royal Society of Chemistry, vol. 144, pp. 2248-2255, Feb. 6, 2019. (Year: 2019).*

* cited by examiner

MICROBIOLOGY TEST CARD

BACKGROUND OF THE INVENTION

The present invention is an improvement upon the invention disclosed in U.S. patent application Ser. No. 14/120,969, filed on Jul. 15, 2014. The disclosure of that prior patent application is incorporated herein by reference both as to it being prior art and as to its disclosure of prior art in the specification and the prosecution history.

The present invention relates generally to apparatus and processes for preparing and examining samples of micro-organisms, and, more particularly, for detecting the presence of harmful bacteria and other micro-organisms.

Various prior devices are known for detecting the presence of coliforms, and other bacteria, by depositing a fluidic test sample onto a card, securing that sample in place on the card in the presence of a growth media by means of a transparent top cover or film, and then allowing the organism to grow for a period of time (with or without the use of a supplemental incubation environment) sufficient for the organism and/or its growth bi-products to react with a chemical media to produce a visual indicia indicating its presence. Often, this visual indicia is a color change observable on the card directly and/or in the presence of ultra violet light. In some prior devices, the cards may use multiple color indicia for verification of the presence of a particular micro-organism or to simultaneously detect multiple different types of micro-organisms.

However, such prior devices have exhibited certain difficulties and/or disadvantages. For example, for various reasons, sometimes relating to the card structures, and sometimes to the specific growth media and visual indicator chemistry, for example, certain types of prior test cards have provided inconsistent, false positive, and/or false negative test results. Also, certain types of prior test cards were not as well suited to automatic detection devices and/or reliable optical scanning as would be desired. Further, such cards sometimes required more expensive production methods than would be desirable, and/or have any unduly short shelf life pending use. In addition, certain prior test cards were not as adaptable to alternative uses as would be desired.

Objectives of the Invention

Accordingly, a primary objective of the present invention is to provide improved test cards for detection of micro-organisms. These improvements include providing microbiology test cards which:
  a. have a less overall cost of manufacture, storage, and use,
  b. increase the economy and/or versatility of card use,
  c. provide more reliable and consistent test results,
  d. accommodate a wide variety of micro-organism types,
  e. increase user safety and convenience, and
  f. have less bulk for waste and are more readily biodegradable.

SUMMARY OF THE INVENTION

These and other objectives of the present invention are achieved by the provision of a card for detecting the existence and/or identity of microbial presence, having a base for receiving thereon a fluidic sample, a transparent cover to overlay the base, formed with a top layer, a bottom layer, and an adhesive layer therebetween, wherein a portion of the bottom layer is formed such that a portion of the adhesive layer is not covered by the bottom layer, and a media applied is to and retained by that portion of the adhesive layer which is not covered by the bottom layer, that media serving to gel the fluidic sample and/or support growth of a micro-organism whose existence and/or identity is being tested by the card. To facilitate manual and/or automated counting of visual indications of micro-organisms, a black ink grid system can be applied which does not diffuse in the presence of the fluidic sample and/or the media, but at the same time which readily is removable from the base when removal is desired.

Other objects, advantages, and novel features of the present invention will become readily apparent from the following drawings and detailed description of certain preferred and alternative embodiments.

BRIEF DESCRIPTION OF THE DRAWINGS

FIG. 2 is a top view of an alternative embodiment of the present invention.

DETAILED DESCRIPTION OF PREFERRED EMBODIMENTS

Figure 1:
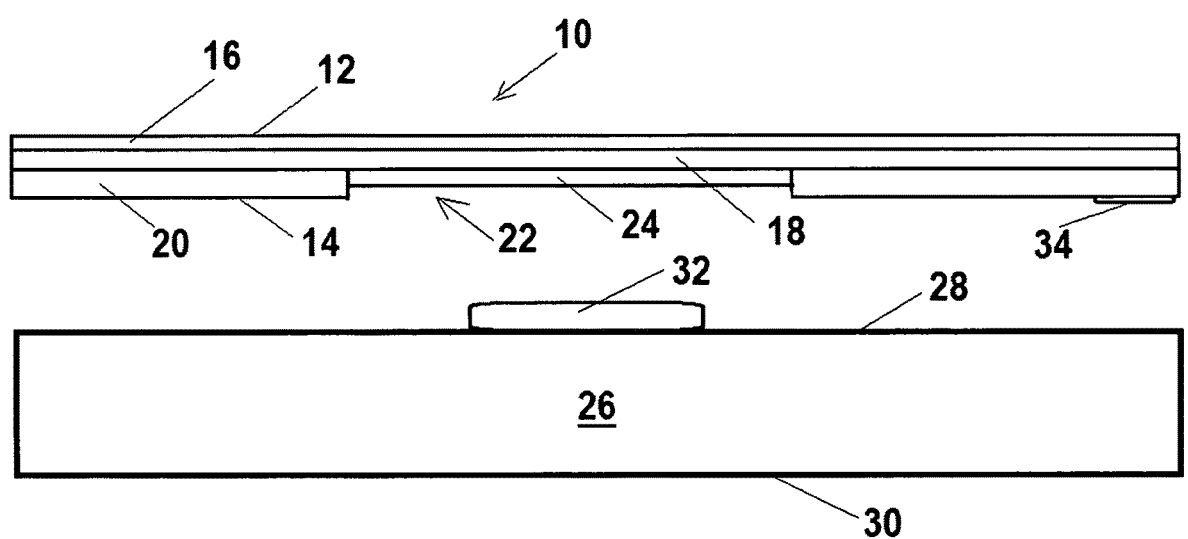
FIG. 1 is schematic cross-sectional, exploded view of a preferred embodiment of the present invention, as taken along line 1-1 of FIG. 2.
Figure 2:
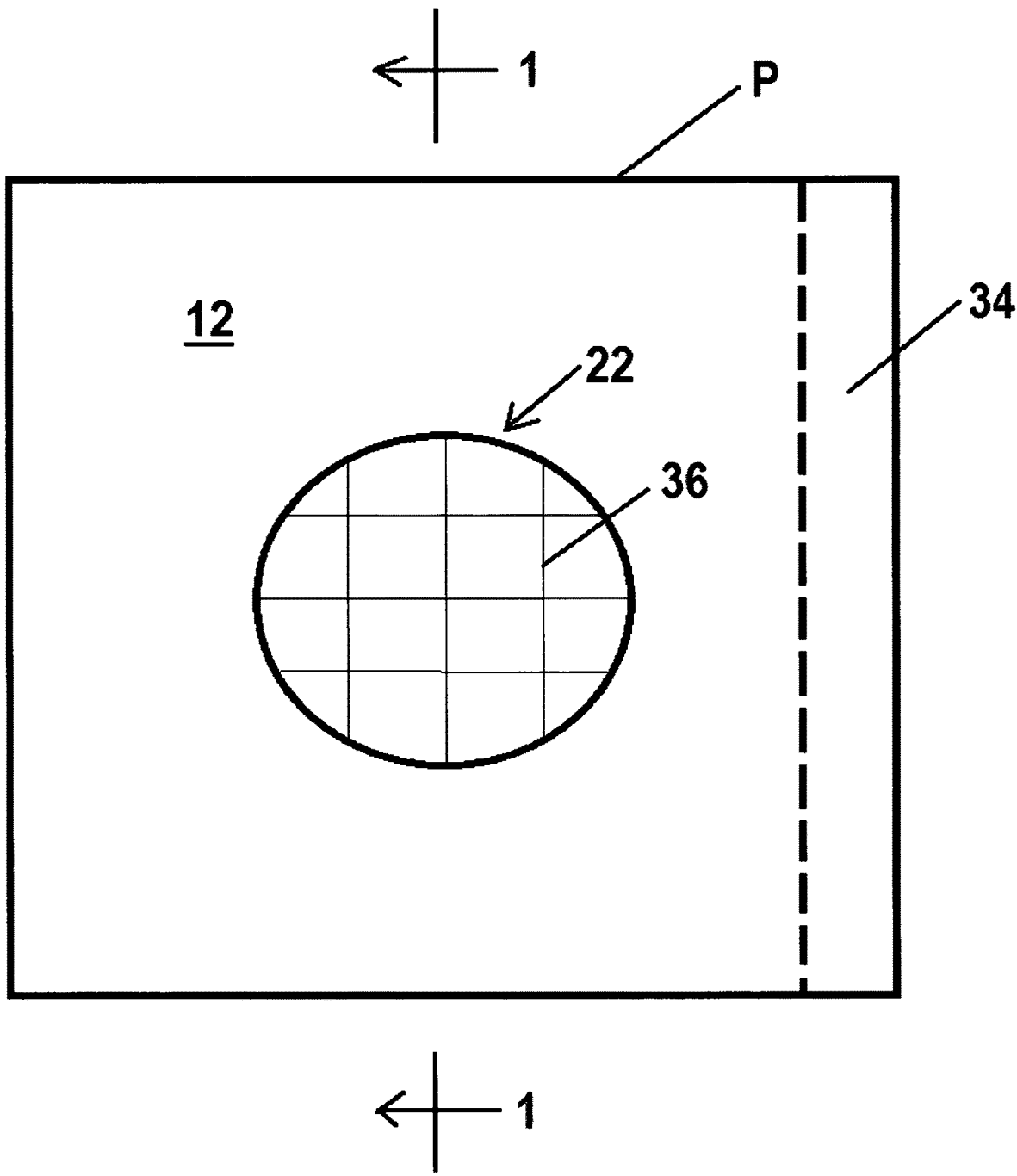
FIG. 2 is a top view of the embodiment of FIG. 1.

The figures show schematically, and in best mode versions, embodiments of the present invention, particularly as applied to test cards for receiving one or more fluidic samples. The drawings are not precisely to scale from one to the next.

The following numbered features of the test card are illustrated in the drawings:
  a cover portion 10, having
    a top surface 12,
    a bottom surface 14,
    a top layer 16, covering
    an adhesive layer 18, covered in part by
    a bottom layer 20, and
      wherein a portion 22 of the bottom layer is formed such that a portion of the adhesive layer is not covered by the bottom layer,
  a media 24 applied to and retained by the portion of the adhesive layer which is not covered by the bottom layer,
  a base portion 26, having
    a top surface 28, and
    a bottom surface 30,
  a periphery P, having
    a portion 34 for securing cover portion 10 to base portion 26 (such as by an adhesive or thermal weld or the like), and
  ink 36 in a grid pattern.

Figure 3:
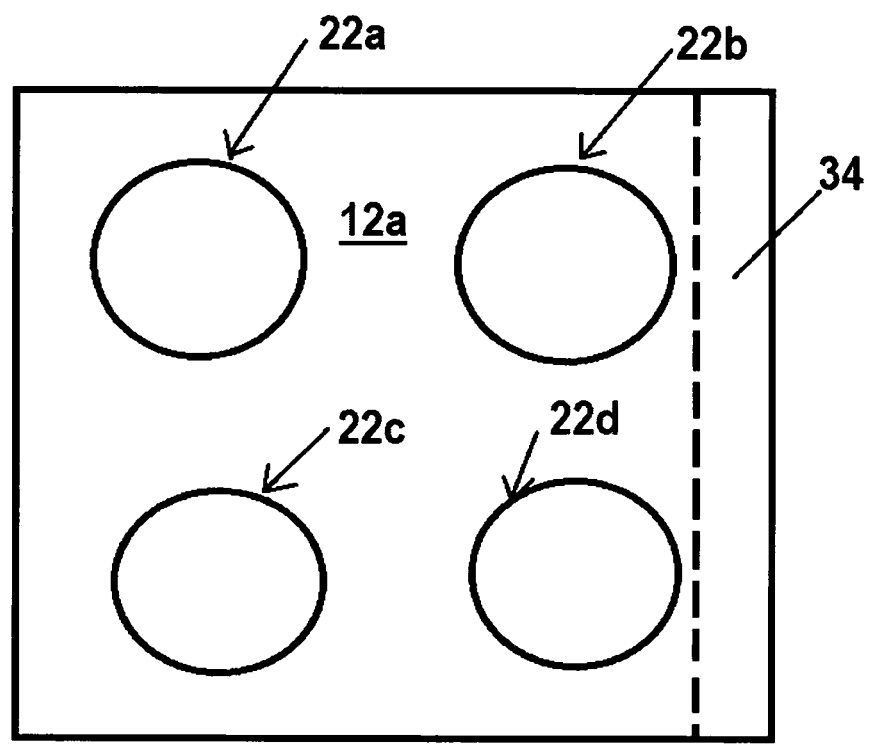

FIG. 3 shows a cover portion of an alternative embodiment of the present invention wherein multiple, separated portions 22a-d of the bottom layer do not cover portions of the adhesive layer.

Briefly, these elements interact as follows:

Base portion 26 is formed to receive a sample to be tested, preferably, but not necessarily entrained in a fluid such as water. Base portion 26 is preferably formed from visibly opaque material. Also, so as to prevent interference with proper dispersion of the resulting gel, base portion is preferably formed from non-absorbent material. In especially preferred embodiments, base portion 26 can be formed from silicone coated paper.

Cover portion 10 is formed to overlay base portion 26, preferably having the same shape and dimensions, so as to present a uniform card appearance. Cover portion 10 is preferably formed from a visibly transparent materials which are sufficiently flexible that most of the cover portion can be moved away from the base portion when the fluidic sample is place on the base portion. Preferably, cover portion 10 is connected to base portion 26 securely along a portion of it periphery so that even though the cover portion can be moved away from the base portion as needed, it can then be readily placed back down upon the base portion, remaining aligned with the periphery of then base portion.

Cover 10 portion is shown as having an adhesive layer 18 applied to top layer 16 and then sandwiched between top layer 16 and bottom layer 20. In production of cover portion 10, bottom layer 20 is scored or die cut prior to application of the bottom layer to adhesive 18. Thereafter, the scored portion 22 is peeled away from the bottom layer to expose a portion of adhesive 18. As shown in the drawings one or more such scored portions 22 or 22a-d can be used as desired. After the scored portion is peeled away, the media 24 is applied to the exposed portion of adhesive 18. In this way, the amount of media needed is reduced and cost savings are available by the present invention. While the shape of portion 22 is shown as circular, any other desired shape can be used in a given embodiment of the present invention. Further, the shape and dimensions of portion 22 can be made to coincide with conventional micropore membrane filters or Whatman®-type filter papers (with fluid applied thereto) in the place of the fluidic test sample, when such are desired for use with the present invention.

In especially preferred embodiments, ink 36 is applied to top surface 12, so that the ink does not interact with either media 24 or fluidic test sample 32. Preferably, ink 36 is formed from a material which resists color diffusion by contact with media 24 and/or fluidic test sample 32, especially in those embodiments where ink 36 is instead applied to top surface 28 of base portion 26. Also, it is preferable that ink 36 be formed from material which is soluble or otherwise removable when in contact with conventional cleaning solvents. An example of a suitable commercially available ink is Film III Ink from Siegwek-Trading Flex, Inc. of Coral Gables, Florida, as described in their technical-specifications posted on their website. In order to reduce costs of manufacturing, the grid of ink 36 need only be applied over the portion of top surface 12 which corresponds to the exposed portion(s) of adhesive layer 18. Preferably, ink 36 is black in color, as opposed to the yellow color used in prior test cards.

Media 24 can be of any conventional composition, as needed according to the nature of the micro-organisms being tested for. Preferably, it will reveal the presence of such micro-organisms by colored areas within the circle of portion 22 under visual or ultra-violet light. Also, preferably, the gelling effect of media 24 with respect to the volume and content of the fluidic test sample is sufficient to confine the dispersion of the fluidic test sample to the circle of portion 22, as the cover portion is applied to the base portion.

In especially preferred embodiments, the test card can be used simultaneously on both sides of base portion 26, since a second cover portion, being a mirror image of cover portion 10, can be applied to bottom surface 30 of base portion 26 in the same manner as cover portion 10 is applied to top surface 28, so as to test another fluidic sample, deposited on bottom surface 30.

Although the present invention has been shown and described herein with respect to certain preferred embodiments and alternative configurations, those were by way of illustration and example only. For example, in especially preferred embodiments, the card has been shown in substantially square formats, but the present invention contemplates other card shapes, such as hexagonal or other rectangular formats. Also, while the card is described for use in connection with fluidic test samples, in some embodiments, solid test samples can be placed on the base portion instead, or the cover portion can be left open for a time to permit air-borne microbial particles, mold spores, and like items to be deposited on the base portion and/or media. Further, rather than scoring bottom layer 20 to create openings therein for exposed portions of adhesive 18, bottom layer 20 can be formed or pre-cut with those openings. Still further, when multiple portions of the adhesive are exposed on the test card, different media can be applied to different exposed portions of the adhesive, so that different types of micro-organisms can be detected simultaneously or verification testing can be done for a single type of micro-organism.

Accordingly, the spirit and scope of the present invention is intended to be limited only by the terms of the appended claims.

What is claimed is:

1. A test card for detecting the presence and/or identity of a microorganism, the test card comprising:
    a base portion having a top surface, the top surface configured to receive a fluidic sample to be tested,
    a cover portion formed to overlay the top surface of the base portion, the cover portion having:
        a periphery,
        a top layer having a top surface,
        a bottom layer to form an interface surface for facing the top surface of the base portion, and
        an adhesive layer between the top layer and the bottom layer,
        wherein a portion of the bottom layer is removed such that a portion of the adhesive layer is exposed and not covered by the bottom layer, and
    a media applied to and retained by the exposed portion of the adhesive layer which is not covered by the bottom layer, wherein the media is retained and confined to a confined area of the exposed portion of the adhesive layer, the confined area being small relative to the interface surface, the media serving to gel the fluidic sample and retain the gelled fluidic sample to a confined surface on the base portion corresponding to the confined area of the exposed portion of the adhesive layer, the confined surface also being small relative to the interface surface to support growth of the microorganism whose presence and/or identity is being tested by the card.

2. The test card according to claim 1 wherein the cover portion is secured along a portion of the periphery to the base portion, and the cover portion is formed from flexible material such that it can be moved away from the base portion sufficiently to allow deposition of the fluidic sample on the base portion without complete removal of the cover portion from the base portion.

3. The test card according to claim 1 wherein the confined area is a circular area located interiorly of the periphery of the cover portion.

4. The test card according to claim 3 wherein the bottom layer includes a scored portion operable to reveal another exposed portion of the adhesive layer wherein the scored portion is removable from the bottom layer prior to application of the media to the circular area to secure the cover portion to the base portion.

5. The test card according to claim 1 wherein the top layer and the adhesive layer of the cover portion are transparent sufficiently to allow visual detection of a color change in the media.

6. The test card according to claim 5 wherein ink in a grid pattern is applied to the top surface of the cover portion, and wherein that ink is formed from a material that resists diffusion upon contact with the fluidic sample and/or the media.

7. The test card according to claim 6 wherein the ink is removably applied to the top surface of the cover portion.

8. The test card according to claim 5 wherein the base portion is formed from visually opaque material.

9. The test card according to claim 8 wherein the base portion is formed from non-absorbent material, with respect to the fluidic sample.

10. The test card according to claim 5 wherein the base portion includes:
   a bottom surface, formed to receive a second fluidic sample to be tested, the test card further comprising a second cover portion operable to overlay the bottom surface of the base portion, the second cover portion having:
     a top layer,
     a bottom layer to form an interface surface for facing the bottom surface of the base portion, and
     an adhesive layer between the top layer and the bottom layer of the second cover portion, wherein a portion of the bottom layer of the second cover portion is removed such that a portion of the adhesive layer is exposed and not covered by the bottom layer of the second cover portion, and
   a second media applied to and retained by the exposed portion of the adhesive layer which is not covered by the bottom layer of the second cover portion, the second media being retained and confined to a second confined area being small relative to the interface surface of the second cover portion, the second media serving to gel the second fluidic sample and retain the gelled second fluidic sample to a second confined surface on the base portion to support growth of the microorganism whose presence and/or identity is being tested by the test card, and
   wherein the second cover portion is secured along a portion of its periphery to the base portion, and the second cover portion is formed from flexible material such that it can be moved away from the base portion sufficiently to allow deposition of the second fluidic sample on the base portion without complete removal of the second cover portion from the base portion.

11. The test card according to claim 1 wherein the bottom layer of the cover portion is formed such that multiple portions of the adhesive layer are exposed and not covered by the bottom layer, and each of the exposed portions of the adhesive layer is separated from other exposed portions of the adhesive layer by the bottom layer to form multiple confined areas for retaining multiple mediums.

12. The test card according to claim 1 further comprising Whatman®-type filter paper to support a fluidic sample applied thereto.

* * * * *